United States Patent [19]

Toomey, Jr.

[11] Patent Number: 4,482,439

[45] Date of Patent: Nov. 13, 1984

[54] ELECTROCHEMICAL OXIDATION OF PYRIDINE BASES

[75] Inventor: Joseph E. Toomey, Jr., Indianapolis, Ind.

[73] Assignee: Reilly Tar & Chemical Corp., Indianapolis, Ind.

[21] Appl. No.: 597,014

[22] Filed: Apr. 5, 1984

[51] Int. Cl.³ .............................................. C25B 3/02
[52] U.S. Cl. ...................................................... 204/78
[58] Field of Search ......................................... 204/78

[56] References Cited

PUBLICATIONS

Fichter, *Helv. Chim. Acta.* 19 1171 (1936).
Yokoyama Bull. Chem. Soc. Jpn. 7 103 (1932).
Sagae, *Heterocycles* 13 321 (1979).

*Primary Examiner*—John F. Niebling
*Attorney, Agent, or Firm*—Woodard, Weikart, Emhardt & Naughton

[57] ABSTRACT

Improved electrochemical oxidations of alkylpyridine bases in which the oxidation is performed by electrolysis in a membrane divided flow cell at a lead dioxide anode and in an aqueous medium comprising sulfuric acid in at least a 1:1 equivalent ratio with the alkylpyridine base in solution. Significant advantages of a commercial and industrial nature are reported over prior static, beaker cell technology.

16 Claims, No Drawings

ELECTROCHEMICAL OXIDATION OF PYRIDINE BASES

BACKGROUND OF THE INVENTION

The subject matter of this invention resides in the field of pyridine chemistry and finds particular utility in providing commercially practicable processes for oxidizing pyridine bases in an electrochemical flow cell.

Substantial research, both past and current, has focused on the oxidation of alkylpyridines to achieve, in addition to possible intermediates, their corresponding pyridinecarboxylic acids. Such acids are quite valuable as chemical intermediates and corrosion inhibitors.

Among the methodologies used, ammoxidation of monoalkylpyridines has been an important route to first producing cyanopyridines which have in turn been hydrolyzed to their carboxylic acid counterparts [P. I. Pollak and M. Windholz, "Heterocyclic Chemistry-Pyridine and its Derivatives," Supplement to Part Three, (R. A. Abramovitch, ed.), p. 273 (1974)]. Although this synthesis requires two discrete steps, each part can proceed in high yield so that the overall reported yields of acids from their hydrocarbon precursors have been good. Additionally molecular oxygen is the oxidizing agent in such cases which affords economical operation. There has also been reported at least some realization as to selectivity of such ammoxidation processes, although yields were generally low and a mixture of products was observed. Frequently, loss of one of the oxidized fragments was noted [N. Kucharczyk, A. Zvakova, Coll. Czech Chem. Commun., 28, 55 (1963)].

Alkylpyridines have also been oxidized by chemical agents such as potassium permanganate ($KMnO_4$). However, these reagents are expensive and have caused excessive oxidation and thereby ring degradation, particularly in the case of polyalkylpyridines [Black, Depp., Coroson, J. Org. Chem., 14, 14 (1949); Chichibabin, Ber., 37, 1373 (1904); Plattner, Keller, Boller, Helv. Chim. Acta, 37, 1379 (1954); Solomon, J. Chem. Soc., 934 (1946)].

Other methodologies include nitric acid oxidation which is reported as a more economical route, although often requiring elevated temperatures and pressures [Bengtsson, Acta Chem. Scand., 9, 832 (1955)]. These harsh conditions can in turn cause decarboxylation or loss of carbon dioxide ($CO_2$) from the resulting product. Catalytic air oxidation has also been reported, but does not appear to have general application either [U.S. Pat. No. 2,437,938], even though selectivity has been achieved in certain cases [U.S. Pat. No. 3,979,400; Mathes, Sauermilch and Klein, Ber, 84, 452 (1951); 86, 584 (1953)]. Still other oxidizing agents have been reported, but all have suffered from lack of generality, excessive cost, and toxicity, pollution, or other problems [U.S. Pat. No. 2,449,906; U.S. Pat. No. 2,513,099; U.S. Pat. No. 2,513,251; Henze, Ber., 67, 750 (1934); Woodward, Badgett and Kaufman, Ind. Eng. Chem., 36, 544 (1944)].

Electrolytic oxidations of certain alkylpyridines have been reported to give reasonable yields in at least some cases. This technique has not achieved the prominence of other methods, however, even though (1) the oxidizing agent is relatively inexpensive, (2) reaction conditions are mild compared to other methodologies, (3) the approach has general application, (4) and prior-experienced toxicity and pollution problems are either nonexistent or minimal. As possible reasons for this lack of acceptance by industry, such electrolytic methods are often difficult to work out experimentally, especially with the polyalkylpyridines, and recognition of their general applicability to fields such as pyridine chemistry has been hampered by conflicting and contradictory reports in the literature. Moreover, advances in cell design technology have lagged seriously behind the existing need and there has been an unwillingness or inability on the part of industry to realize the potential significance and advantages of this technology and to effect its use in the field of pyridine chemistry.

For example, although electro-oxidations have been reported for producing the three isomeric monocarboxylic acids from their monoalkylpyridine precursors, such reports have achieved only moderate yields of less than 45% in all cases except nicotinic acid in which a 70% yield was reported. Processes have also been reported for some of the six isomeric pyridinedicarboxylic acids (notably, quinolinic acid from quinoline in addition to lutidinic acid from 2,4-lutidine and isocinchomeronic acid from 2-methyl-5-ethylpyridine), but with similar failings. Moreover, no processes have been reported to applicant's knowledge for the electrochemical production of 2,6-diacid (dipicolinic), 3,5-diacid (dinicotinic), 2,3-diacid (quinolinic) from 2,3-lutidine, or 3,4-diacid (cinchomeronic).

More importantly, all such reports were strictly on a laboratory scale in which the electrolyzers used were simply static, beaker cell designs. As such, their usefulness is restricted to either small bench-scale preparations (0.01-1 kg) or the analytical arena, and they are not viable in a commercial or industrial setting. These beaker cells have also always used porous dividers to separate the anode and cathode compartments. The non-selective permeability of these porous dividers cause mixing of the separated solutions leading to material and efficiency losses. Attempts to use porous ceramic dividers on a commercial scale are also hampered by the mechanical fragility of such devices. Moreover, there is no suggestion in these or any other references known to applicant that alternative cell geometries and techniques which have commercial potential could be adapted for use in the field of pyridine chemistry.

With regard to selectivity during electro-oxidation, the applicant is aware of only two published reports which deal with an attempt to isolate such intermediate-stage oxidation products. Both dealt with nicotine oxidation to nicotinic acid and are conflicting. Fichter and Stenzl [Helv. Chim. Acta, 19, 1171 (1936)] reported no intermediate-stage oxidation products could be found while Yokoyama [Bull. Chem. Soc. Jpn., 7, 103 (1932)] reported hydroxynicotine and decomposition products were detected. Additionally, the applicant is aware of a report of oxidation of methylpyridines and the respective N-oxides by electrogenerated superoxide ion [H. Sagae, M. Fujihira, H Lund and T. Osa, Heterocycles, 13, 321 (1979)]. The presumed intermediate-stage aldehydes were not detected and the conclusion was that, if such materials are formed, further oxidation is rapid and no observable concentration of aldehyde is formed.

SUMMARY OF THE INVENTION

Applicant's invention addresses this problem in proving for the first time the viability of performing electrochemical oxidations of alkylpyridine bases in commercially practicable flow cells. Applicant's flow cells are not restricted as to a particular design geometry and can feature batch or continuous processing in an industrial environment, depending upon factors such as electrolyzer feed preparation, considerations of product separation and purification, user need, and the like. Use of a high-surface-area anode has proven of benefit in at least certain oxidations, and applicant's yields and current efficiencies have been marked improvements over the prior art as have the economics of the reactions based on applicant's flow cell design. The ability to control selectivity during electro-oxidation and isolate intermediate-stage oxidation products in modest yield is also believed to be a marked improvement over the prior art where such products are either undetectable or formed in conjunction with a variety of decomposition products.

Related objects and advantages of the present invention will be apparent from the following description.

DESCRIPTION OF THE PREFERRED EMBODIMENT

For the purposes of promoting an understanding of the principles of the invention, reference will now be made to the preferred embodiment and specific language will be used to describe the same. It will nevertheless be understood that no limitation of the scope of the invention is thereby intended, such alterations and further modifications in the device, and such further applications of the principles of the invention therein being contemplated as would normally occur to one skilled in the art to which the invention relates.

In accordance with the above summary, applicant has discovered and proven that electrochemical oxidations of alkylpyridine bases having the formula

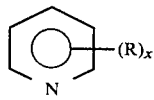

wherein:
x = 1-3; and
R = —CH$_3$,
    a primary or secondary alkyl group having about 2-6 carbon atoms,
    a cycloalkyl group having about 3-6 carbon atoms,
    an aralkyl group of the formula [—(CH$_2$)$_n$—aryl] where n = 1-3,
    —(CH$_2$)$_m$COR' or —(CH$_2$)$_m$CHOHR' where m = 0-5 and R' = H, or
    an alkyl group having about 1-6 carbon atoms, or a cycloalkyl, aryl or aralkyl group having about 3-10 carbon atoms;
and wherein two adjacent R groups on the ring taken together may be a fused cycloalkyl or a fused aryl group, are successfully performed in a flow cell having definite commercial and industrial applications. This was accomplished in applicant's preferred embodiment at a lead dioxide anode using an ion-exchange membrane to separate compartments in the cell and further using an aqueous electrolyte solution comprising sulfuric acid present in at least a 1:1 equivalent ratio with the alkylpyridine starting material in solution.

In this regard, the phrase "electrochemical oxidation" is meant to include all possible variations as to reaction conditions and the like which are known to those of ordinary skill in the art to which applicant's invention pertains. The only exceptions to this relate to any specific conditions or features which have shown to be required from applicant's testing to date, which are further detailed hereinbelow. In addition, the phrase "flow cell" is meant to be restrictive only in the sense of excluding any cell consisting of a tank, beaker or container of similar function which is employed as a mixed or unmixed electrolyzer and which is limited by the inability to achieve a substantially plug flow of electrolyte in the reactor, by the inability to obtain a high space-time yield consistent with more sophisticated electrolyzers, or by the inability to effectively use ion-exchange membranes which are most often conveniently made and purchased in sheet form. In so doing, the phrase "flow cell" is meant to include all other electrolyzers which may employ either a batch or continuous mode of operation with a substantially plug flow of solution through the reactor and which can be conveniently constructed as filter-press, disc-stack or concentric tube cells. For example, this includes both batch reactors where the electrolyte is continually recirculated through a closed loop as well as continuous processes where steady-state conditions are approached and/or product is continually removed and the electrolyte regenerated for further use. No cell geometries are excluded from the scope and intent of applicant's invention so long as they comply with these fluid flow characteristics.

In each case, the choice of reactor and operational mode for use with applicant's invention varies with the particular chemistry involved both as to reaction conditions which must be observed as well as other factors affecting product separation, purification, and the like. Applicant's preferred electrochemical flow cell to date is his own filter press cell which is the subject of U.S. patent application, Ser. No. 477,529, filed Mar. 21, 1983 and entitled FILTER PRESS ELECTROCHEMICAL CELL WITH IMPROVED FLUID DISTRIBUTION SYSTEM. Accordingly this prior application is hereby incorporated herein by reference in its entirety as to all pertinent and relevant aspects thereof relating to prior cell design technology and to the disclosure and understanding of applicant's preferred flow cell as used herein.

As to specific materials or conditions, applicant's preferred electro-oxidations to date have been performed at a lead dioxide anode supported on a base such as lead, titanium or carbon. An aqueous electrolyte solution has been used comprising sulfuric acid in at least a 1:1 equivalent ratio with the alkylpyridine precursor in solution. An ion-exchange membrane has been used in all cases, but whether it was cation- or anion-permeable has depended upon the particular reaction involved as specified in the examples which follow. As to preferred conditions of applicant's reactions to date, temperatures have preferably been maintained between about 10°-90° C., with a range of about 30°-70° C. being most preferred. Current densities in the cell have been maintained between about 0.1-200 mA/cm$^2$ while most preferred has been a range of about 2-50 mA/cm$^2$. As to the electrolyte solution itself, the preferred concentration of alkylpyridine in solution has varied between about 0.5-35 wt% with a concentration range of about 10-20 wt% being most preferred for the majority of electro-oxidations applicant has performed thus far.

The advantages shown to exist with applicant's preferred flow cell arrangement are many, including those previously discussed as well as features such as the ability to continually remove heat from the cell as, for example, by circulating the electrolyte through a heat exchanger or similar apparatus. Continual product removal and regeneration of the electrolyte solution is also possible using standard and accepted techniques known to those of ordinary skill in the art with regard to the particular reaction involved. Specific electro-oxidations have also proven to be substantially more efficient than prior art reports with the use a high-surface-area (HSA) anode in which to conduct the oxidation. Examples of such HSA electrodes are wire meshes, metal particles such as lead spheres or other packing material, and those discussed in more detail in applicant's electrochemical cell application previously incorporated hereinabove by reference.

An additional feature of applicant's work has been the discovery that selective or partial electrochemical oxidation can be achieved with a particular alkylpyridine base by controlling the amount of charge passed through the cell during electrolysis. This feature has no absolute limitations, but varies with the particular chemistry involved and the intermediate product desired. The starting place for determining such factors is knowledge of the chemical reaction taking place. An estimate of the total current required for exhaustive or complete oxidation to the corresponding pyridinecarboxylic acid can then be calculated from an overall material balance for a given operating period and with the assumption of 100% current efficiency. This material balance is also necessarily made using a projected feed composition and rate, percentage conversion of reactants, and operational mode. During subsequent operation, as shown in several of the examples which follow, the total quantity of charge is expressed as a measure of ampere hours (or alternately Faradays) per mole. The charge is passed until the desired or maximum conversion to the intermediate-stage oxidation product is achieved. This is followed by isolation and recovery of the desired intermediate oxidation product using conventional procedures. Stopping the electrolysis reaction in this manner has been shown in certain of applicant's examples to lead to significant commercial products, and this can be true even though yields may not be as great as with a completed reaction. They are nonetheless within the scope and contemplation of applicant's invention herein.

Reference will now be made to the specific examples which follow in order to further describe and to show the features of applicant's preferred embodiment and its advantages and improvements over the prior art. In this regard, where possible, specific reference is made in the examples to known prior art processes in order to better understand and distinguish applicant's invention herein. It is further understood that these examples are representative only, and that such additional embodiments and improvements of the same are within the contemplation and scope of applicant's invention as would occur to someone of ordinary skill in this art.

EXAMPLE 1

Picolinic Acid from 2-Picoline

The anolyte was first prepared from the following weight ratios of materials: 2-picoline (1.0), sulfuric acid (1.5), sodium sulfate (0.4), and water (3.3). The catholyte used was 15 wt% aqueous NaOH. The electrolytes were placed in their respective reservoirs and pumped through a divided flow cell having an anion-exchange membrane and a packed-bed lead dioxide anode consistent with that disclosed in U.S. Ser. No. 477,529, which has been previously incorporated herein by reference. Charge was then passed at 20 mA/cm$^2$ until 8 F/mole was obtained. The anolyte was then neutralized to the isoelectric pH for picolinic acid and all volatiles removed. The resultant solid was extracted with hot toluene, the insoluble portion removed by filtration while hot, and the picolinic acid crystallized to obtain an 80% yield of material. The current efficiency was 67%. At subsequent experiments using 80 mA/cm$^2$, the current efficiency dropped to 59%. At 3 mA/cm$^2$, the current efficiency and yield rose to ~90% each. Alternately, a cation-exchange membrane divided flow cell was used with the catholyte being aqueous sulfuric acid containing sodium bisulfate. The isolated yield and current efficiency were about 70% for each at 20 mA/cm$^2$. In this particular case, a planar PbO$_2$ anode gave similar results. In addition, if the ratio of equivalents of sulfuric acid to pyridine base was significantly less than 1:1, then the yield of oxidation products dramatically decreased. Ratios higher than 2:1 were usually necessary to achieve the most beneficial results.

These results experienced by applicant were marked improvements over literature reports of yields approximating 40% [M. Yokoyama, *Bull. Chem. Soc. Japan*, 7, 69 (1932); E. Ochiai, S. Okuda, *J. Pharm. Soc. Japan*, 70, 156 (1950)] the first prior art reference also using a lead dioxide anode and sulfuric acid/water electrolyte. Both references were restricted to a beaker cell having no economic value for industrial production. This same product was similarly reported in poor yields using electrogenerated superoxide ion [H. Sagae, M. Fijihara, H. Lund, t. Osa, *Heterocycles*, 13, 321 (1979)].

EXAMPLE 2

Nicotinic Acid from 3-Picoline

The electrolytic methodologies for picolinic acid in Example 1 were used here by substituting 3-picoline for the 2-picoline precursor. This gave a 65% yield and 70% current efficiency at 10 mA/cm$^2$ current density when either the cation- or anion-exchange membrane process was used. Similar results were obtained in a flow cell having only planar PbO$_2$ anodes without packing. As with Example 1, these results equalled or surpassed literature reports as to 65–70% yields and current efficiencies of about 55%, but in a static beaker cell electrolyzer [M. Kulka, *J. Am. Chem. Soc.*, 68, 2472 (1946); V. G. Khomyakov, S. S. Kruglikov, *Trdy Moskov. Khim.-Technol. Inst. im D. I. Mendeleeva*, (25), 178 (1957); V. G. Khomyakov, S. S. Kruglikov, V. M. Berezovsku, *Zhur. Obshchei Khim.*, 28, 2898 (1958); V. G. Khomyakov, S. S. Kruglikov, N. A. Izgaryshav, *Doklady Akad. Nauk SSSR*, 115, 557 (1957); S. S. Kruglikov, V. G. Khomyakov, *Tr. Mosk. Khim-Teknol. Inst.*, (32), 194 (1961)]. It is noted that platinum anodes are reported to have given even poorer yields and efficiencies [E. Blasiak, L. Piszczek, A. Tramer, *Chem. Stosowana* XII, 3A, 309 (1968)].

EXAMPLE 3

Isonicotinic Acid from 4-Picoline

The same electrolytic methodologies were used here as in Example 1 by substituting 4-picoline for 2-picoline. A 75% yield and 70% current efficiency were obtained at 10 mA/cm$^2$ current density at a packed-bed anode. This result surpassed literature reports of 42–46% yields at 28% current efficiencies using a beaker cell design [J. Alamelin, K. S. Talitha, K. Radhakrishnaumurthi, S. Chidambaram, M. S. V. Pathy, H. V. K. Udupa, *Trans. Soc. Advan. Electrochem. Sci. Technol.*, 6 (3), 97 (1971); A. Ito, K. Kawada, *Ann. Rept. Takamine Lab.*, 5, 14 (1953)]. Such references also show that the addition of electron "carriers," or indirect oxidation methods, was ineffective as was the use of a platinum anode, although one report indicated platinum was as effective as lead dioxide. Superoxide ion also gave poor yields [H. Sague, M. Fugihira, H. Lund and T. Osa, *Heterocycles*, 13, 321 (1979)].

EXAMPLE 4

Oxidation of 2-Ethylpyridine

The anolyte consisted of the following weight ratios of materials: 2-ethylpyridine (1.0), sulfuric acid (1.5), sodium sulfate (0.1), and water (3.5). The catholyte was 10 wt% sufluric acid. A flow cell as in Example 1 was used having a cation-exchange membrane and a $PbO_2$ packed-bed anode. Charge was passed (6 F/mole) at 25 $mA/cm^2$ current density. The anolyte was worked up as before and gave a 30% yield of picolinic acid and a 40% yield of 2-acetylpyridine. Passing more charge through the anolyte before work up increased the yield of acid significantly. A flow cell with an anion-exchange membrane could also be used where the catholyte was 10 wt% sodium hydroxide. Varying the weight parts of components in the anolyte changed the ratio of ketone to carboxylic acid as did switching from one membrane type to the other. Varying the total charge passed also increased or decreased the ketone yield thereby confirming the aspect of applicant's invention that such intermediates can be produced.

EXAMPLE 5

Oxidation of 3-Ethylpyridine

The same procedure was used as for 2-ethylpyridine in Example 4, and gave a 35% yield of carboxylic acid at 6F/mole charge passed. Again, the major product was a ketone, 3-acetylpyridine (45%), and passing more charge significantly increased the yield of the carboxylic acid.

EXAMPLE 6

Oxidation of 4-Ethylpyridine

The procedure in Example 4 was used to give a 15% yield of carboxylic acid and a 39% yield of 4-acetylpyridine at 6F/mole charge passed. A 45% yield of acid was realized at 8F/mole charge being passed. Further yield increases were possible. This result contrasted with the prior art oxidation of 4-ethylpyridine to isonicotinic acid which was reported in about 75% yield, but involved the use of a beaker cell, a noble metal anode, and a highly-corrosive electrolyte (nitric acid) with current efficiency being reported somewhat low, at about 50% [A. Ito, K. Kawada, *Ann Rept Takamine Lab.*, 5, 14 (1953)]. In this reference, when a $PbO_2$ anode was used with the nitric acid, a 50% yield of carboxylic acid was obtained but when sulfuric acid replaced the nitric acid, the $PbO_2$ anode was completely ineffective.

EXAMPLE 7

Quinolinic Acid from 2,3-Lutidine

The cation-exchange membrane flow cell and catholyte in Example 4 were used with an anolyte composed of the following weight parts: 2,3-lutidine (1.0), sulfuric acid (3.0), and water (5.0). Charge was passed until no significant amount of 2,3-lutidine was present in the anolyte. Partial neutralization of the sulfuric acid precipitated quinolinic acid in 60% yield and 65% current efficiency. When an anion-exchange membrane was used, only a 20% yield of the diacid was realized at the same level of charge being passed.

EXAMPLE 8

Lutidinic Acid from 2,4-Lutidine

The procedure for quinolinic acid in Example 7 was used except that 2,4-lutidine was substituted for 2,3-lutidine. A 40% yield and 35% current efficiency were achieved. This result was significantly better than the single-known literature report which used a beaker cell and exhibited a very poor yield of 22% and current efficiency even worse at 15% [V. G. Khomyakov, S. S. Kruglikov and L. I. Kazakova, *Tr. Mosk. Khim.-Tekhnol. Inst.* (32), 189 (1961)]. In applicant's attempt to duplicate this literature report in a beaker cell, similar dismal results were obtained thereby confirming the improvement achieved by applicant's preferred reaction in a flow cell.

EXAMPLE 9

Oxidation of 3,5-Lutidine

The above procedure in Example 7 was used and yielded 35% dinicotinic acid and about 5% 5-methylnicotinic acid at 7.5 F/mol. When an anion-exchange membrane was used with dilute NaOH as the catholyte, selectivity for the monoacid was greatly increased and a 20% yield of 5-methylnicotinic acid was obtained at 6 F/mole.

EXAMPLE 10

Isocinchomeronic Acid from 2-Methyl-5-Ethylpyridine

The procedure for quinolinic acid in Example 7 was used to give the corresponding diacid as the major product, with a 40% yield at 100% theoretical charge being passed. Increasing the charge passed was also found to increase this yield as significant quantities of intermediate-stage oxidation products were further oxidized to the diacid product. The only known report of electro-oxidizing this dialkylpyridine was again conducted in a beaker cell, and exhibited only a fair yield (45%) and poor current efficiency (30%) for the complete oxidation product, isocinchomeronic acid [L. D. Borkhi, *Khim. Geterotsikl. Soedin.* (10), 1362 (1970)].

EXAMPLE 11

Isocinchomeronic Acid from 2-Methyl-5-Butylpyridine

The above procedure in Example 7 was used and yielded 30% of the diacid at 100% theoretical charge passed.

EXAMPLE 12

Quinolinic Acid from Quinoline

When quinoline was substituted for 2,3-lutidine in the procedure in Example 7, a 75% yield and 60% current efficiency were achieved. Increasing charge passed beyond that necessary to convert all the quinoline was tested, and it did not increase the diacid yield significantly.

These results differed from literature references which were restricted to beaker cells having no economic value for industrial production. In addition, the use of an ion-exchange membrane reduced losses of materials from the anode compartment and raised material balances and recoveries. The use of catalytic amounts of V₂O₅ were also avoided as was expensive noble metal anodes [M. Kulka, J. Am. Chem. Soc., 68 2472 (1946); V. G. Khomyakov, S. S. Kruglikov, *Trdy Moskov. Khim.-Technol. Inst. im D. I. Mendeleeva*, (25) 178 (1957); V. G. Khomyakov. S. S. Kruglikov, V. M. Berezovsku, *Zhur. Obshchei Khim.*, 28, 2898 (1958); V. G. Khomyakov. N. G. Bakhchisaraits'yan, M. Ya. Tioshin. S. S. Kruglikov, L. J. Kazakova, *Tr. Mosk. Khim.-Technol. Inst.*, (32), 249 (1961); J. C. Cochran, W. F. Little, *J. Org. Chem.*, 26, 808 (1961); M. Yokoyama, K. Yamamoto, *Bull. Chem. Soc. Japan*, 18, 121 (1943); L. D. Borkhi, V. G. Khomyakov; *Khim. Geterotsikl. Soedin.*, 1967 (1), 167; V. G. Khomyakov. L. D. Borkhi, *Tr. Vses. Nauch.-Issled. Inst. Khim. Reaktivov Osobo Chist. Khim. Veshchestv*, 29, 226 (1966); V. G. Khomyakov, L. D. Borkhi, V. G. Brudz, N. E. Khomutov, V. G. Khomyakov, *Khim. Geterotsikl. Soedin.*, 1967 (1), 112; L. D. Borkhi, ibid, 1979 (10), 1362; L. D. Borkhi, Et al., *Tr. Vses, Nauch-Issled., Inst. Khim. Reaktivov Osobo Chist. Khim. Veschestv*, 1970 (32) 122; J. B. Conn, J. Van de Kamp, U.S. Pat. No. 2,453,701 (1948); J. B. Conn, U.S. Pat. No. 2,512,483 (1950)].

EXAMPLE 13

Picolinic Acid from 2-Ethanolpyridine

The procedure used was the same as for 2-picoline in Example 1 with the cell being divided with a cation-exchange membrane and having a packed-bed anode. The yield of acid was 75% and current efficiency 80% at 10 mA/cm² current density.

EXAMPLE 14

Isonicotinic Acid from 4-Pyridylcarbinol

The procedure for 4-picoline in Example 4 was used with the appropriate substitution of pyridine starting material. A 95% yield of carboxylic acid was achieved at 90% current efficiency.

EXAMPLE 15

Niacin from 3-Acetylpyridine

The procedure for 2-picoline in Example 1 was used with the appropriate change in pyridine starting material. A 91% yield and 87% current efficiency were realized.

EXAMPLE 16

Isonicotinic Acid from 4-Pyridylacetone

The procedure for 2-picoline in Example 1 was used with 4-pyridylacetone, and resulted in an 85% yield of isonicotinic acid.

EXAMPLE 17

6-Methylpicolinic Acid from 2,6-Lutidine

The procedure for 2-ethylpyridine in Example 4 was used where the 2,6-lutidine replaced the 2-ethylpyridine. When a cation-exchange membrane was used, a 10% yield of moncarboxylic acid was realized. The major product was the diacid.

EXAMPLE 18

Intermediate Oxidation Products from 2-Methyl-5-Ethylpyridine

The above procedure in Example 4 was carried out to give a mixture of products consisting of 2-methyl-5-acetylpyridine (1), 5-acetylpicolinic acid (2), 5-ethylpicolinic acid (3), and isocinchomeronic acid (4). The ratios and yields of each compnent varied according to the type of membrane used, amount of charge passed, and current density. A typical result would be 18% (1), 19% (2), 3% (3), and 40% (4) at 12 F/mole and 25 mA/cm². Very similar results were obtained when 2-methyl-5-butylpyridine was substituted for the 2-methyl-5-ethylpyridine, where the products were now 5-(2-methylpyridyl)propyl ketone, 5-(2-carboxypyridyl)propyl ketone, fusaric acid, and isocinchomeronic acid.

EXAMPLE 19

2-Benzoylpyridine

The procedure for 2-ethylpyridine in Example 4 was used where 2-benzylpyridine replaced the 2-ethylpyridine. A 78% yield of the corresponding ketone intermediate was obtained at 5 F/mol charge being passed and 50 mA/cm² current density.

EXAMPLE 20

Dimethyl(4-pyridyl)carbinol

The same procedure as in Example 4 was used where 4-isopropylpyridine replaced the 2-ethylpyridine. After 4 F/mol of charge was passed, a 20% yield of the carbinol intermediate was obtained.

I claim:

1. In an electrochemical oxidation of an alkylpyridine base having the formula

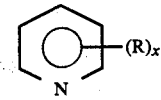

wherein:
x=1-3; and
R=—CH₃,
    a primary or secondary alkyl group having about 2-6 carbon atoms,
    a cycloalkyl group having about 3-6 carbon atoms,
    an aralkyl group of the formula [—(CH₂)$_n$—aryl] where n=1-3, —(CH₂)$_m$COR' or —(CH₂)$_m$CHOHR' where m=0-5 and R'=H, or
    an alkyl group having about 1-6 carbon atoms, or a cycloalkyl, aryl or aralkyl group having about 3-10 carbon atoms, and wherein two adjacent R groups on the ring taken together may be a fused cycloalkyl or a fused aryl group,
the improvement comprising performing said oxidation in a flow cell having an ion-exchange membrane divider at a lead dioxide anode and in an aqueous medium comprising sulfuric acid in at least a 1:1 equivalent ratio with said alkylpyridine base in solution.

2. The reaction in claim 1 in which said oxidizing of one of the electroactive groups on said alkylpyridine base by electrolysis is complete to its corresponding pyridinecarboxylic acid, and additionally comprising the step of recovering said resulting acid product from the electrolyte.

3. The reaction in claim 2 in which said alkylpyridine base is selected from the group consisting of:
   2-picoline;
   3-picoline;
   4-picoline;
   2-ethylpyridine;
   3-ethylpyridine;
   4-ethylpyridine;
   2,3-lutidine;
   2,4-lutidine;
   3,5-lutidine;
   2-methyl-5-ethylpyridine;
   2-methyl-5-butylpyridine;
   quinoline;
   2-ethanolpyridine;
   4-pyridylcarbonol;
   3-acetylpyridine; and
   4-pyridylacetone.

4. The reaction of claim 1 in which said oxidizing of one of the electroactive groups on said alkylpyridine base by electrolysis is partial by passing an amount of charge through said flow cell which is less than that needed to complete said oxidation, and additionally comprising the step of recovering the intermediate oxidation product from the electrolyte.

5. The reaction of claim 4 in which said alkylpyridine base is 2-ethylpyridine and said recovered product is 2-acetylpyridine.

6. The reaction of claim 5 in which said pyridine base is 3-ethylpyridine and the recovered product is 3-acetylpyridine.

7. The reaction of claim 6 in which said alkylpyridine base is 4-ethylpyridine and the recovered product is 4-acetylpyridine.

8. The reaction of claim 7 in which said alkylpyridine base is 3,5-lutidine and the recovered product is 5-methylnicotinic acid.

9. The reaction of claim 8 in which said alkylpyridine base is 2,6-lutidine and the recovered product is 6-methylpicolinic acid.

10. The reaction of claim 9 in which said alkylpyridine base is 2-methyl-5-ethylpyridine and the recovered products are 2-methyl-5-acetylpyridine, 5-acetylpicolinic acid, and 5-ethylpicolinic acid.

11. The reaction of claim 10 in which said alkylpyridine base is 2-methyl-5-butylpyridine and the recovered products are 5-(2-methylpyridyl)propyl ketone, 5-(2-carboxypyridyl)propyl ketone and fusaric acid.

12. The reaction of claim 11 in which said alkylpyridine base is 2-benzylpyridine and the recovered product is 2-benzoylpyridine.

13. The reaction of claim 12 in which said alkylpyridine base is 4-isopropylpyridine and the recovered product is dimethyl(4-pyridyl)carbinol.

14. The reaction of claim 2 in which the sulfuric acid is present in at least a 2:1 equivalent ratio with said alkylpyridine base in solution.

15. The reaction of claim 4 in which the sulfuric acid is present in at least a 2:1 equivalent ratio with said alkylpyridine base in solution.

16. The reaction of claim 1, the improvement further comprising passing only sufficient charge through said flow cell to produce a yield of at least about 10% of an intermediate product not expected in the final oxidation, and recovering said intermediate oxidation product from the electrolyte.

* * * * *